United States Patent [19]

Hope

[11] Plant 4,744

[45] Jun. 16, 1981

[54] KALANCHOE NAMED PUEBLO

[75] Inventor: Claude Hope, Cartago, Costa Rica

[73] Assignee: Pan-American Plant Company, West Chicago, Ill.

[21] Appl. No.: 150,590

[22] Filed: May 16, 1980

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Chas W. Rummler

[57] ABSTRACT

A new and distinct variety of kalanchoe plant particularly distinguished by its unique orange-yellow flowers supported by rigid upright stems in tightly clustered panicles above and between shiny dark green leaves. This plant is intended for year-around four and six inch pot production and has a ten to twelve week flowering response to photoperiod control. It has a rapid and vigorous growth habit with caespitose branching, abundant foliage, and a profuse production of flowers.

2 Drawing Figures

BACKGROUND OF THE NEW PLANT

My new variety of kalanchoe plant originated as a seedling resulting from breeding efforts carried on by me at Cartago, Costa Rica, with the object of producing new and better varieties for the kalanchoe market. The geneology of this new plant is as follows:

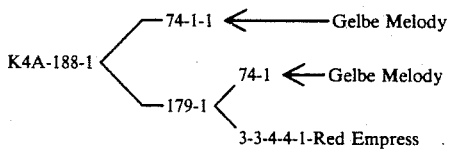

The seeds of this mating were collected in February 1977 and sown in June 1977. The selection of this plant for propagation was made on Jan. 4, 1978, and first propagation was done by me with cuttings of the selected plant on Jan. 23, 1978, in Cartago, Costa Rica. Subsequent propagation through successive generations has shown that the novel characteristics of this new variety hold true from generation to generation and appear to be firmly fixed. This new kalanchoe variety is now being propagated by cuttings at West Chicago, Ill., and at Parrish, Fla.

DESCRIPTION OF THE DRAWINGS

My new kalanchoe cultivar is illustrated by the accompanying drawings, of which sheet 1 is a full color photographic print showing the growth and flower display characteristics of the plant, and sheet 2 is a print of a close-up photograph of the flowers of this plant which has been hand-painted to show the true color of the flowers as specified.

DESCRIPTION OF THE NEW PLANT

The following is a detailed description of the new kalanchoe cultivar based upon observations made of greenhouse grown plants in the Fall of 1979 at West Chicago, Ill., the color designations being according to The R.H.S. Colour Chart published by The Royal Horticultural Society of London, England.

THE PLANT

Origin: Seedling.

Parentage:
- *Seed parent.*—Gelbe Melody.
- *Pollen parent.*—A seedling of Gelbe Melody × Red Empress.

Classification:
- *Botanic.*—*Kalanchoe blossfeldiana.*
- *Commercial.*—Flowering Kalanchoe Pot Plant.

Form: Bush.

Shape: Upright vase shape.

Height: Variable.

Growth: Strong, vigorous and upright.

Growth rate: Rapid.

Branching character: Caespitose.

Foliage:
- *Quantity.*—Abundant.
- *Leaf size.*—Large, about 30 to 90 mm. long and 30 to 70 mm. wide.
- *Shape.*—Ovate with sinuate margin.
- *Texture.*—Smooth and fleshy.
- *Surface aspect.*—Glossy.
- *Ribs and veins.*—Netted.
- *Color.*—Upper side — 137A. Under side — 137D.
- *Petioles.*—Length — 1 to 8 mm.

THE BUD

Size: Medium with variations in both diameter and length.

Shape: Long pointed.

Opening rate: Normal.

Color of petals:
- *When sepals first divide.*—White.
- *When petals begin to unfurl.*—17A to 17D.

Sepals: Four in number surrounding the receptacle and hooded over the bud. When flowers open, the sepals stand up and have an awl shape appearance.
- *Color.*—Inside surface — 138D. Outside surface — 138D.

Calyx:
- *Shape.*—Pear-shaped.
- *Size.*—Small.
- *Splitting.*—Calyx does split.
- *Aspect.*—Smooth.

Peduncle:
- *Length.*—Variable.
- *Aspect.*—Smooth.
- *Character.*—Rigid and erect.
- *Color.*—138B.

THE FLOWER

Blooming habit: Intermittent.
Recommended flowering: Year around with photoperiod control.
Response: 10 to 12 weeks.
Blooms: Plant blooms profusely.
*Size of flowers.*—Small.
*Borne.*—In a panicle.
*Shape.*—When bloom first opens — cup-shaped. When bloom matures — somewhat flattened.
Petalage:
*Number of petals.*—Four or five.
*Arrangement.*—Sympetalous and imbricated in funnel form.
*Form.*—Generally oval with rounded apex and entire margin.
*Texture.*—Soft.
*Appearance.*—Satiny.
*Color.*—Upper side body — 17A. Upper side base — 14C. Reverse side — 17D.
Peduncle:
*Character.*—Strong and upright.
*Length.*—Variable.
*Color.*—138B.
Effect of weather: Very little.
Persistence: Flowers hang on and dry.
Fragrance: None.
Lasting quality: Four to six weeks on blooming plant.

REPRODUCTIVE ORGANS

Stamens: Number — eight in didynamous arrangement.
*Anthers.*—Size and color: insignificant.
*Filaments.*—Length and color: insignificant.
*Pollen.*—Color — yellow.
Pistils: Number — four.
*Styles.*—Length and color: insignificant.
*Stigmas.*—Green, turning white.
Ovaries: Four superior ovaries.

This kalanchoe variety is quite unique in character and is particularly distinguished by its orange-yellow flowers displayed in closely massed panicles supported by rigid caespitose stems above the dark green shiny leaves. This new kalanchoe cultivar is particularly adapted for year-around four and six inch pot production under photoperiod control and has a substantially uniform ten to twelve week flowering response. The new plant has a vigorous, upright and rapid growth habit with abundant foliage and a profuse production of flowers which have a four to six week lasting quality on the blooming plant.

I claim:

1. A new and distinct variety of kalanchoe plant, substantially as herein shown and described, characterized by its orange-yellow flowers displayed in panicles supported by rigid stems and clustered above and between dark green shiny leaves, the plant having a strong, vigorous and rapid growth habit and a profuse production of flowers.

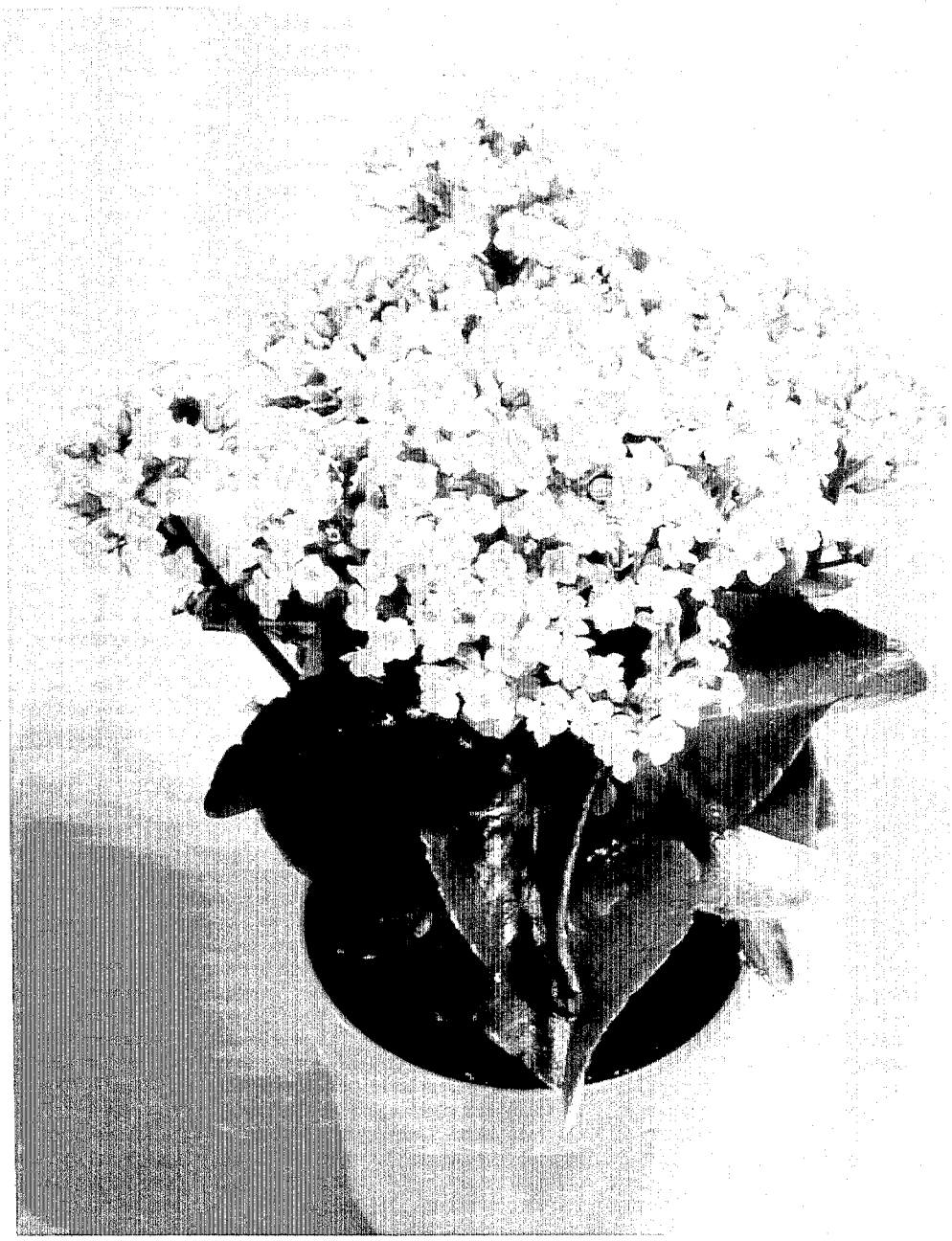

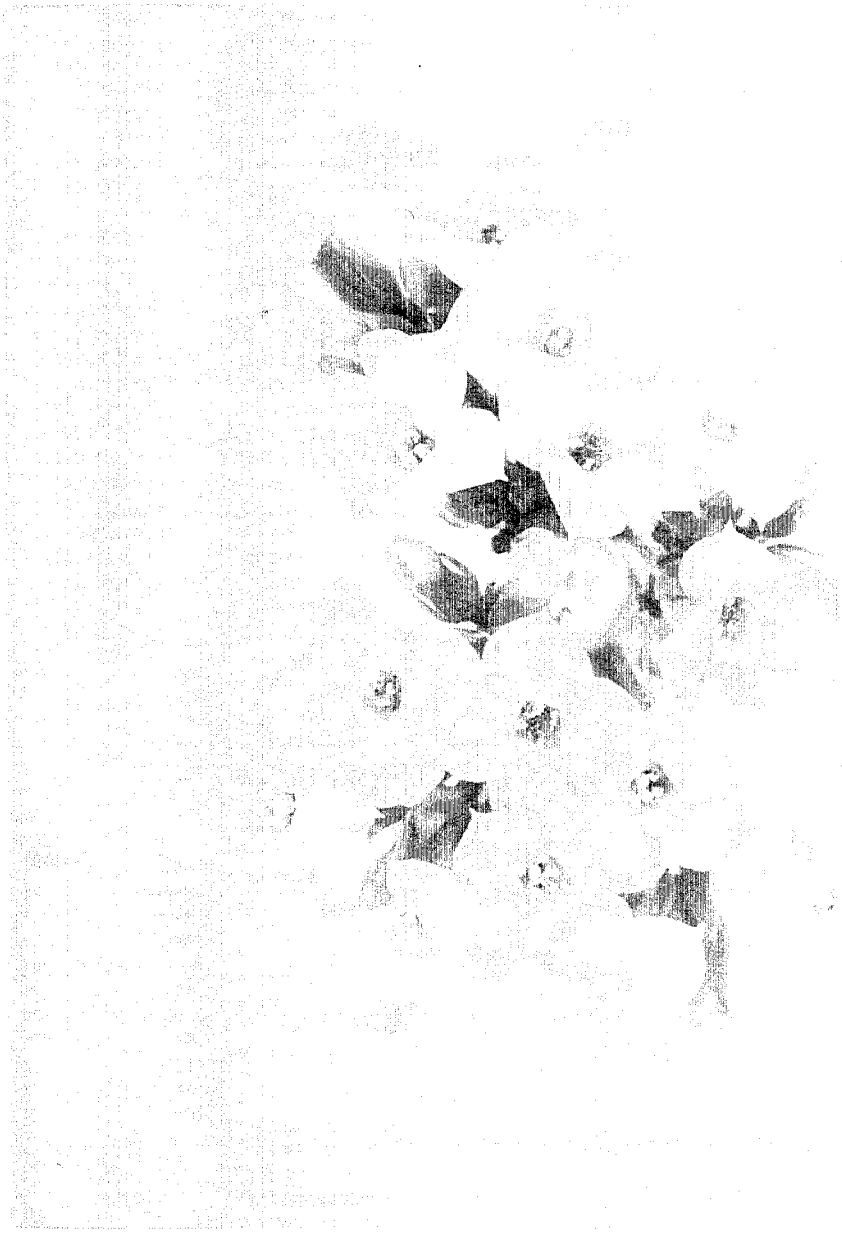

* * * * *